US011587655B2

United States Patent
Molkenthin et al.

(10) Patent No.: US 11,587,655 B2
(45) Date of Patent: Feb. 21, 2023

(54) METHOD FOR MONITORING BREASTFEEDING EVENTS AND PROVIDING FEEDBACK

(71) Applicants: Brittany Molkenthin, Canterbury, CT (US); Jayme Coates, Canterbury, CT (US)

(72) Inventors: Brittany Molkenthin, Canterbury, CT (US); Jayme Coates, Canterbury, CT (US)

(*) Notice: Subject to any disclaimer, the term of this patent is extended or adjusted under 35 U.S.C. 154(b) by 169 days.

(21) Appl. No.: 15/931,049

(22) Filed: May 13, 2020

(65) Prior Publication Data
US 2021/0358583 A1    Nov. 18, 2021

(51) Int. Cl.
| | |
|---|---|
| *G16H 15/00* | (2018.01) |
| *G16H 50/20* | (2018.01) |
| *G16H 10/60* | (2018.01) |
| *A61B 5/00* | (2006.01) |
| *G16H 80/00* | (2018.01) |
| *G16H 20/60* | (2018.01) |

(52) U.S. Cl.
CPC ........... *G16H 15/00* (2018.01); *A61B 5/7292* (2013.01); *A61B 5/742* (2013.01); *A61B 5/746* (2013.01); *G16H 10/60* (2018.01); *G16H 20/60* (2018.01); *G16H 50/20* (2018.01); *G16H 80/00* (2018.01); *A61B 2503/04* (2013.01)

(58) Field of Classification Search
CPC ........ G16H 15/00; G16H 10/60; G16H 20/60; G16H 50/20; G16H 80/00; A61B 5/7292; A61B 5/742; A61B 5/746; A61B 2503/04
See application file for complete search history.

(56) References Cited

U.S. PATENT DOCUMENTS

| | | | | |
|---|---|---|---|---|
| 8,280,493 | B2* | 10/2012 | Kolberg | A61B 5/4288 600/476 |
| 11,064,924 | B2* | 7/2021 | Woltjer | A61B 8/4477 |
| 2008/0097169 | A1* | 4/2008 | Long | A61B 5/103 600/301 |
| 2015/0223755 | A1* | 8/2015 | Abir | A61B 5/746 600/300 |
| 2016/0183602 | A1* | 6/2016 | Rider | A61M 1/06 450/36 |
| 2019/0242816 | A1* | 8/2019 | Conner | G01F 25/20 |
| 2020/0384171 | A1* | 12/2020 | Tian | A61B 5/0053 |
| 2021/0282744 | A1* | 9/2021 | Refai | A61B 8/4472 |

* cited by examiner

*Primary Examiner* — Ryan W Sherwin
(74) *Attorney, Agent, or Firm* — Murtha Cullina LLP; Anthony P. Gangemi

(57) ABSTRACT

A method of monitoring a breastfeeding of a user that includes providing at least one detector that measures a first data of a breastfeeding event, receiving a second data from the user and processing the first data and the second data to create a lactation transfer report. The method communicates the lactation transfer report to a user device and/or a device accessible by one or more experts and provides feedback to the user based on an evaluation of the lactation transfer report by the one or more experts. The first data includes the time of the breastfeeding event, a length of the breastfeeding event and/or a rate of filling of the breastfeeding event. The user device receives the second data in the form of additional breastfeeding information from the user.

12 Claims, 7 Drawing Sheets

METHOD FOR MONITORING BREASTFEEDING EVENTS AND PROVIDING FEEDBACK

BACKGROUND

New mothers rely on prior knowledge and a brief hospital stay in order to be able to proficiently nurse their babies. The current trend is towards shorter maternity stays is based often on monetary needs rather than prioritizing the health and well-being of the baby and family. Although insurance companies are required to extend coverage for normal deliveries to forty-eight hours following the birth of the child, this is still an insufficient amount of time to establish proficient nursing from the mother to the child in many instances.

Currently, medical assessments are performed at follow-up visits. Early follow-up visits focusing on breastfeeding are integral to make sure that the baby is nursing effectively. Many doctors require the mother to bring the baby to appointments with some professionals offering to visit the baby in the home. If the mother has issues with breastfeeding efficiency, experts are available at many hospitals or doctors' offices. Access to these experts is limited to mothers with adequate insurance and/or those that can afford the follow-up appointments and have the ability to travel with the newborn baby to specific locations. Telephone check-ins are generally available, but there is a lack of options for continued breastfeeding monitoring and feedback for new mothers that cannot afford and/or cannot accommodate traveling with the newborn.

There is a need in the art for an application and method of monitoring the breastfeeding events of a new mother and newborn baby and providing communication with an expert for evaluation, to provide advice and follow-up care.

SUMMARY

There is disclosed herein a method of monitoring lactation transfer information from a user to a baby. The method includes receiving first data from one or more detectors that measure lactation transfer information of a breastfeeding event between the user and the baby; receiving second data from a user device; processing the first data and the second data to create a lactation transfer report; communicating the lactation transfer report to a user device and/or a device accessible by one or more experts and providing feedback to the user based on the first data, the second data and/or the lactation transfer report. The first data includes a time of the breastfeeding event, a length of the breastfeeding event and/or a rate of filling of the breastfeeding event. The user device receives the second data from the user.

In one embodiment, the second data includes a side of the last feeding, a mood of the user, a mood of the baby, an additional sensation information, a weight of the baby, a confidence level of the user, a sleep schedule of the baby, an amount of milk pumped, an amount of milk supplemented, a post-partum depression rating, a rating of support received from the community and a photograph.

In one embodiment, the additional sensation information includes let-down information, latching information or pain information.

In one embodiment, the first data includes an initial volume of milk in a stomach of the baby, a volume of milk transferred to the baby and/or a residual amount of milk in stomach of the baby.

In one embodiment, the feedback includes providing an emergency contact, a physician name and/or a lactation support contact name.

In one embodiment, the method also includes automatically selecting relevant information from a database based on the first data, the second data and/or the lactation transfer report and providing the relevant information to the user and/or the one or more experts.

In one embodiment, the method also includes recording the first data, the second data and/or the lactation transfer report in a medical record of the user.

In one embodiment, the method also includes providing a notification to the one or more experts and/or the user based on the first data, the second data and/or the lactation transfer report.

In one embodiment, the method also includes scheduling and/or altering an appointment of the user and one or more experts based on the first data, the second data and/or the lactation transfer report.

In one embodiment, user device has a display and the user directly communicates with the one or more experts through the display of the user device.

In one embodiment, the method also includes communicating the first data, the second data and/or the lactation transfer report to a designated recipient selected by the user.

In one embodiment, the user device is a smart phone, tablet computer, desktop computer, PDA, or the like.

In one embodiment, the method also includes evaluating a nutritional content of the breastfeeding event and providing recommendations based on a difference between the nutritional content of the breastfeeding event and the nutritional content of an expected breastfeeding event.

There is also disclosed herein a method of monitoring lactation transfer information from a user to a baby including receiving first data from one or more detectors that measure a lactation transfer information of a breastfeeding event between the user and the baby; receiving second data from a user device; processing the first data and the second data to create a lactation transfer report and creating a predictive model based on the first data, the second data and/or the lactation transfer report. The first data includes a time of the breastfeeding event, a length of the breastfeeding event and/or a rate of filling of the breastfeeding event. The user device receives the second data from the user.

In one embodiment, the predictive model generates an expected next feeding time for the baby.

In one embodiment, the predictive model generates an additional feeding time for the baby and/or a recommended supplement time for the baby. The additional feeding time establishes a time needed to meet a normal feeding amount.

In one embodiment, the predictive model estimates a fullness of the baby.

In one embodiment, the predictive model diagnoses and predicts cluster feedings, growth spurts, illness and/or teeth growing.

There is also disclosed herein method of monitoring lactation transfer information from a user to a baby including receiving a first data from one or more detectors that measure a lactation transfer information of a breastfeeding event between the user and the baby; receiving second data from a user device; processing the first data and the second data to create a lactation transfer report; communicating the lactation transfer report to a user device and/or a device accessible by one or more experts; generating a feedback indicator based on the first data, the second data, the lactation transfer report, an input received from the user and/or an input received from the one or more experts and providing the feedback indicator to the user device. The feedback indicator indicates normal filling rate, abnormal filling rate, normal time of feeding, abnormal time of feeding, normal volume of feed, abnormal volume of feed, normal frequency of feed and/or abnormal frequency of feed. The first data includes a time of the breastfeeding event, a length of the breastfeeding event and/or a rate of filling of the breastfeeding event. The user device receives the second data from the user.

In one embodiment, the method also includes notifying the user and/or one or more experts with a warning based the first data, the second data and/or the lactation transfer report.

In one embodiment, the warning is an initial warning or an imminent trouble warning. The initial warning advises the user or expert to seek additional support. The imminent trouble warning provides recommendations for triage and emergency support.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

It is recognized that certain limitations and features described in the present disclosure may need to be modified or removed in order to be in compliance with applicable local laws. By way of example, in the United States, certain limitations and features may need to be modified or removed in order to be in compliance with the Health Insurance Portability and Accountability Act (HIPAA).

Figure 1:
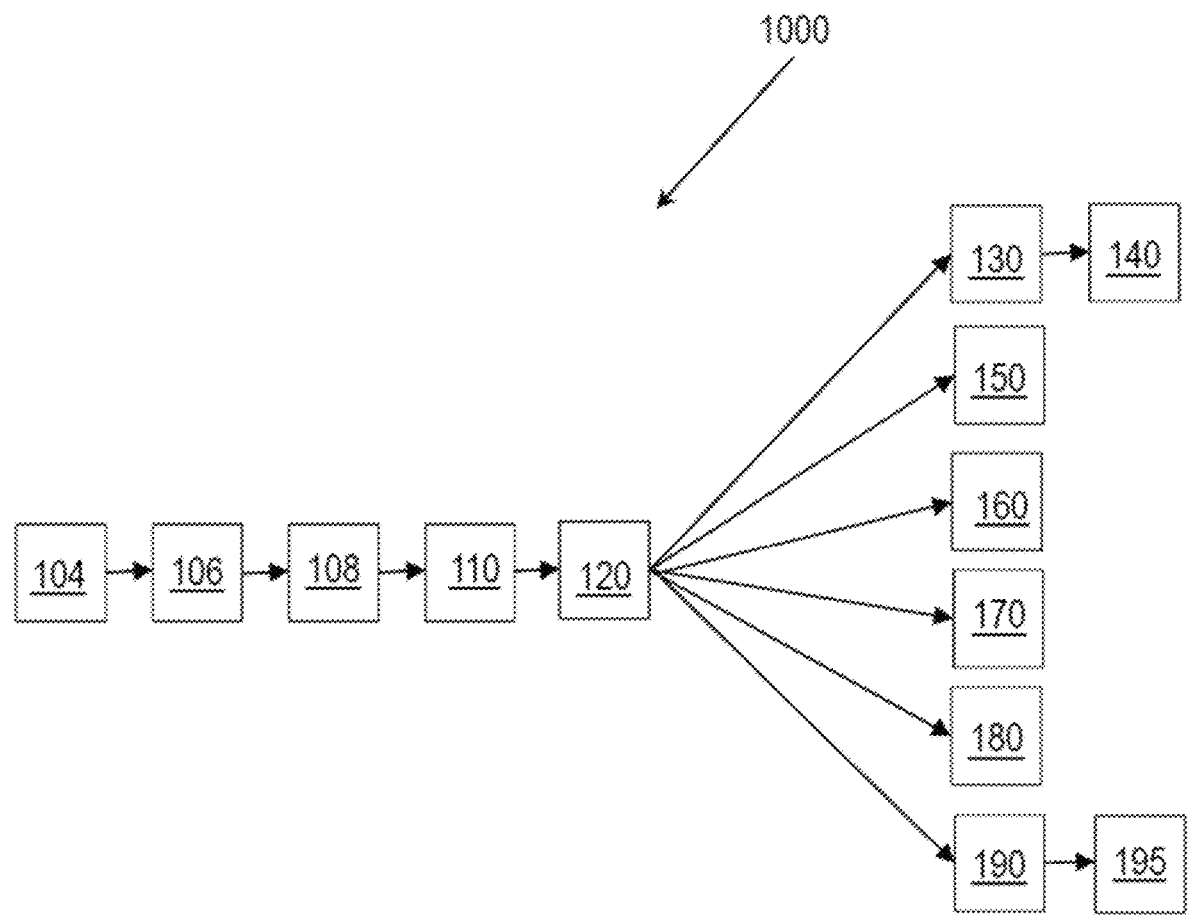
FIG. 1 is a chart of a method of monitoring a breastfeeding of a user according to some embodiments of the present disclosure.

Referring now to FIG. 1, a method of monitoring a breastfeeding of a baby by a user (i.e., a mother) is generally denoted as reference numeral 1000. Generally, a user 100 is a mother that is using the method 1000 disclosed herein. Anyone else the mother chooses to share her information with may be included as a user 100 for the purposes of the present disclosure. At 102, the method 1000 includes providing at least one detector 200 (depicted in FIG. 2) configured to measure a lactation transfer information of a breastfeeding event between the user 100 and the baby. At 104, the detector 200 receives a first data 210 from the at least one detector that measures the lactation transfer between the user 100 and the baby. The first data 210 indicates a time of the breastfeeding event, a length of the breastfeeding event and/or a rate of filling of the breastfeeding event. The detector 200 measures the breastfeeding event by using an infrared light source and an infrared light sensor, a volumetric sensor, an ultrasonic sensor, a voltage sensor, etc. and combinations thereof. At 106, the method 1000 receives a second data 605 from a user device 600. In one embodiment, the at least one detector 200 is provided by an alternative source and the method 1000 receives the first data 210 from the at least one detector 200.

In the embodiment depicted in FIGS. 1-6, the user 100 inputs the second data 605 into the user device. In the some embodiments, the second data 605 is the side of the last feeding, a mood of the user 100, a mood of the baby, an additional sensation information, a weight of the baby, a confidence level of the user, a sleep schedule of the baby, an amount of milk pumped, an amount of milk supplemented, an emergency contact, a physician name, a lactation support contact name, a post-partum depression rating, a rating of support received from the community and/or a photograph. The additional sensation information includes let-down information, latching information or other relevant pain information.

Referring to FIG. 1, the method 1000 processes the first data 210 and the second data 605 to create a lactation transfer report at 108. At 110, the method 1000 communicates the lactation transfer report to at least one of a user device 600 and a device 400 accessible by one or more experts. The device 400 accessible by the one or more experts includes a device similar in functionality to the user device 600 and/or a device already in use by the one or more experts. Experts include, but are not limited to, a doctor, a clinician, a breastfeeding/lactation consultant or other healthcare professional with specialized knowledge in the field of breastfeeding and nursing of a newborn and groups thereof. At 120, the method 1000 provides feedback to the user 100 based on an evaluation of the lactation transfer report by the one or more experts. This feedback gives the user 100 a support staff one the mother is at home for telehealth purposes, providing ongoing care and support to the mother. In some embodiments, the feedback provides suggestions for relevant support groups.

In some embodiments, the first data 210 includes the volume of breast milk consumed, an initial volume of milk in a stomach of the baby, a volume of milk transferred to the baby and/or a residual amount of milk in stomach of the baby. In some embodiments, a breastfeeding proficiency 310 of the user is established by comparing the measured breastfeeding events and the breastfeeding event types to historical breastfeeding events 112 or expected breastfeeding events 114.

Figure 2:
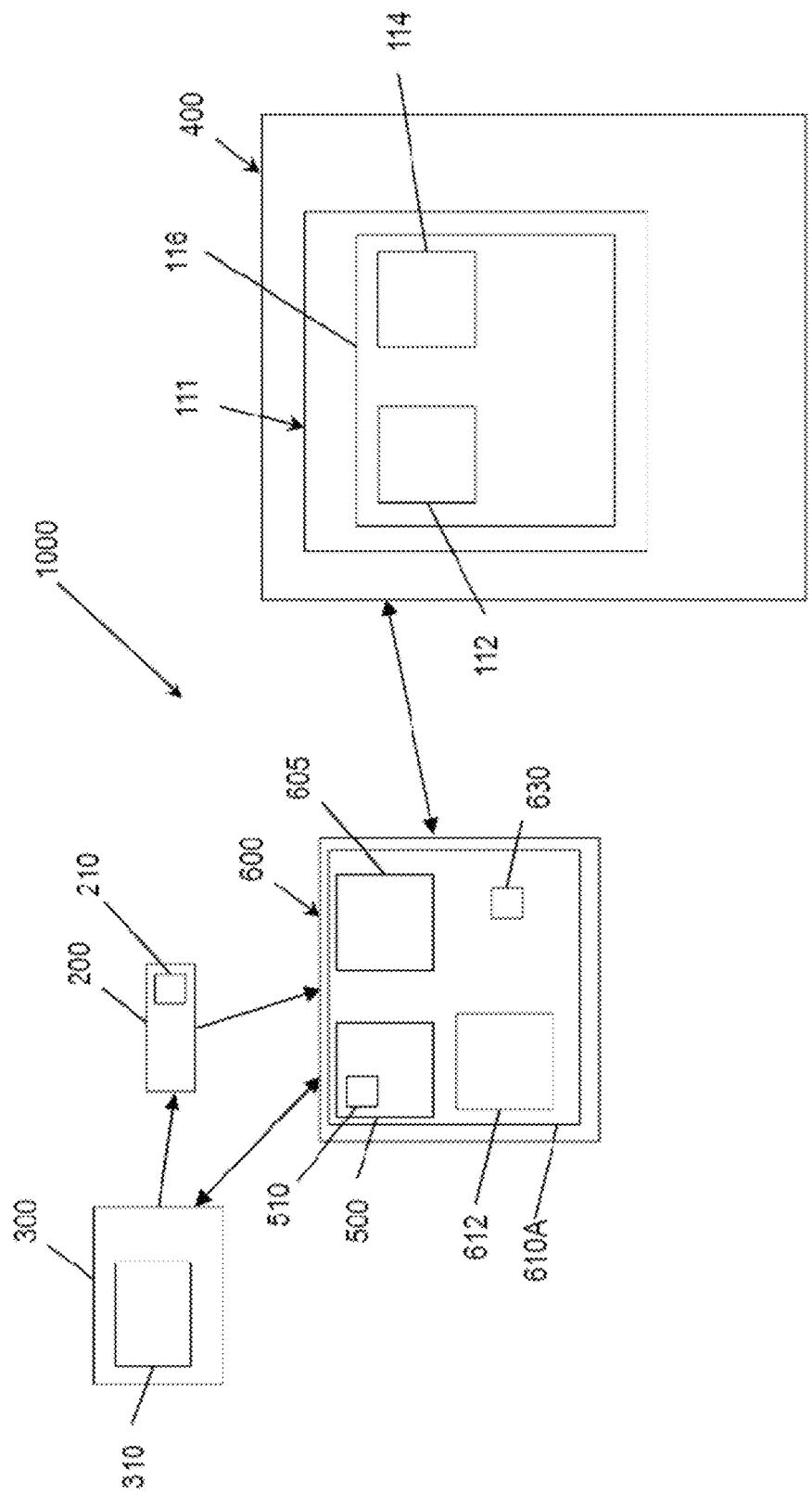
FIG. 2 is a schematic drawing of a system for monitoring a breastfeeding of a user according to the method of some embodiments of the present disclosure.

At 102, the method 1000 provides a non-transitory computer storage medium 500 in communication with the at least one detector 200 and encoded with one or more computer programs 510 (depicted in FIG. 2) for outputting the first data 210 in the form of the breastfeeding event time, length, or frequency and storing the first data 210 on the computer storage medium 500. Non-transitory computer storage medium 500 includes one or more processing units and system memory. The non-transitory computer storage medium 500 is any suitable type of storage for storing executable code of the one or more computer programs 510 to facilitate acquisition and analysis of breastfeed data and export such data, as is known to those having skill in the art. In some embodiments, the historical breastfeeding events 112 and/or the expected breastfeeding events 114 are stored on the computer storage medium 500. In the embodiment depicted in FIG. 2, the historical breastfeeding events 112 and/or the expected breastfeeding events 114 are provided by the device 400 of the one or more experts. Referring to FIG. 2, the detector 200 connects to a user device 600 in the form of a computer device that contains the non-transitory medium 500. The user device 600 provides a display 610A to the user 300 and connects the user 100 to device 400 of the one or more experts. In some embodiments, the user device 600 or the device 400 is a smart phone, tablet computer, desktop computer, PDA, or any other device that displays information and provides for communication. In some embodiments, a processor of the user device 600 executes applications and/or programs to alternate between a number of displays 610A, 610B, 610C, 610D, and 610E, to provide the information and/or the functionality as discussed in detail herein. The user device 600 allows live chat and video chats with physicians, nurses, lactation staff, etc. on an as needed basis. The user device 600 also connects to email, SMS, etc. to indicate if there is a critical message.

Referring to FIG. 1, the method 1000 automatically selects relevant information from a database based on the first data, the second data and/or the lactation transfer report at 130. At 140, the method provides the relevant information to the user and/or the one or more experts. At 150, the method records the first data 210, the second data 605 and/or the lactation transfer report in a medical record of the user. At 160, the user 100 directly communicates with the device 400 of one or more experts through the display 610A of the user device 600. In some embodiments, the user 100 chooses a designated recipient that the user agrees to share access to all or part of the first data, the second data, and/or the lactation transfer report.

In some embodiments, the method 1000 provides a notification to the device 400 of at least one of the one or more experts and the user 300 based on a breastfeeding proficiency of the user 300. In some embodiments, the method 1000 schedules or alters an appointment between the user 300 and one or more experts 400. The method 1000 selects relevant information 116 from a database 111 at 160 based on the first data 210, the second data 605 and/or the lactation transfer report of the user 300 and provides the relevant information 116 to the user 300 and the device 400 of the one or more experts. In some embodiments, the method 1000 includes incorporating the first data 210, the second data 605 and/or the lactation transfer report into the historical breastfeeding events or expected breastfeeding events in the database 111.

The method 1000 provides the first data 210 and the second data 630 to the experts and data in the form of help from the experts or directed information to users 300 to support their roles as new mothers. The method 1000 coordinates care among mothers and their doctors, clinicians, etc. The method 1000 provides access to additional breastfeeding data sets as stored in the database 111 that is relevant information 116 for various types of users 300 including new mothers and experts including lactation consultants and doctors. The method 1000 notifies clinicians, alters follow-up schedules of the clinicians and the users 300, and selects relevant information 116 in an automated fashion for delivery to new mothers and experts.

Figure 3A:
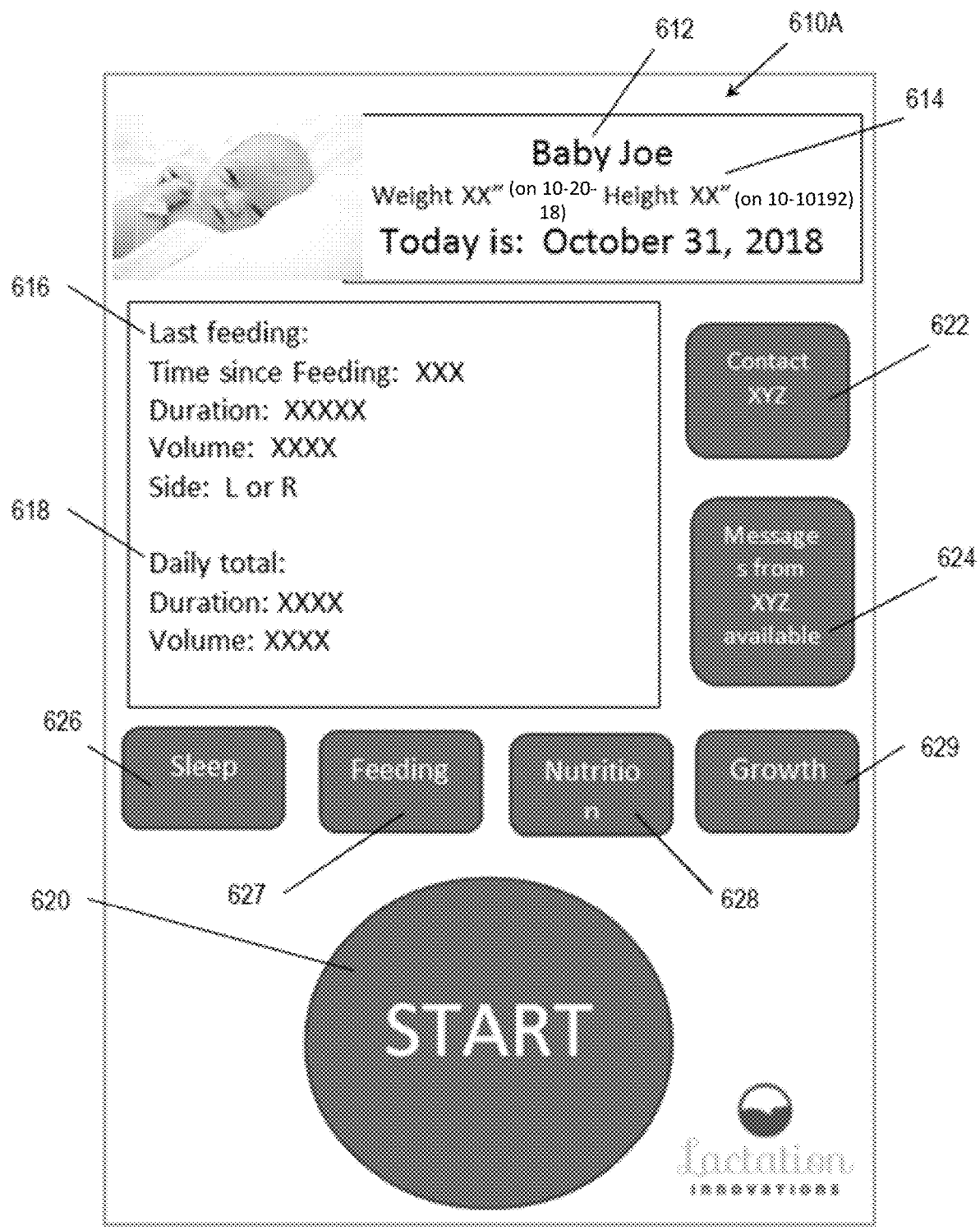
FIG. 3A is a front view of a display of a user device incorporating the method of FIG. 1.
Figure 3B:
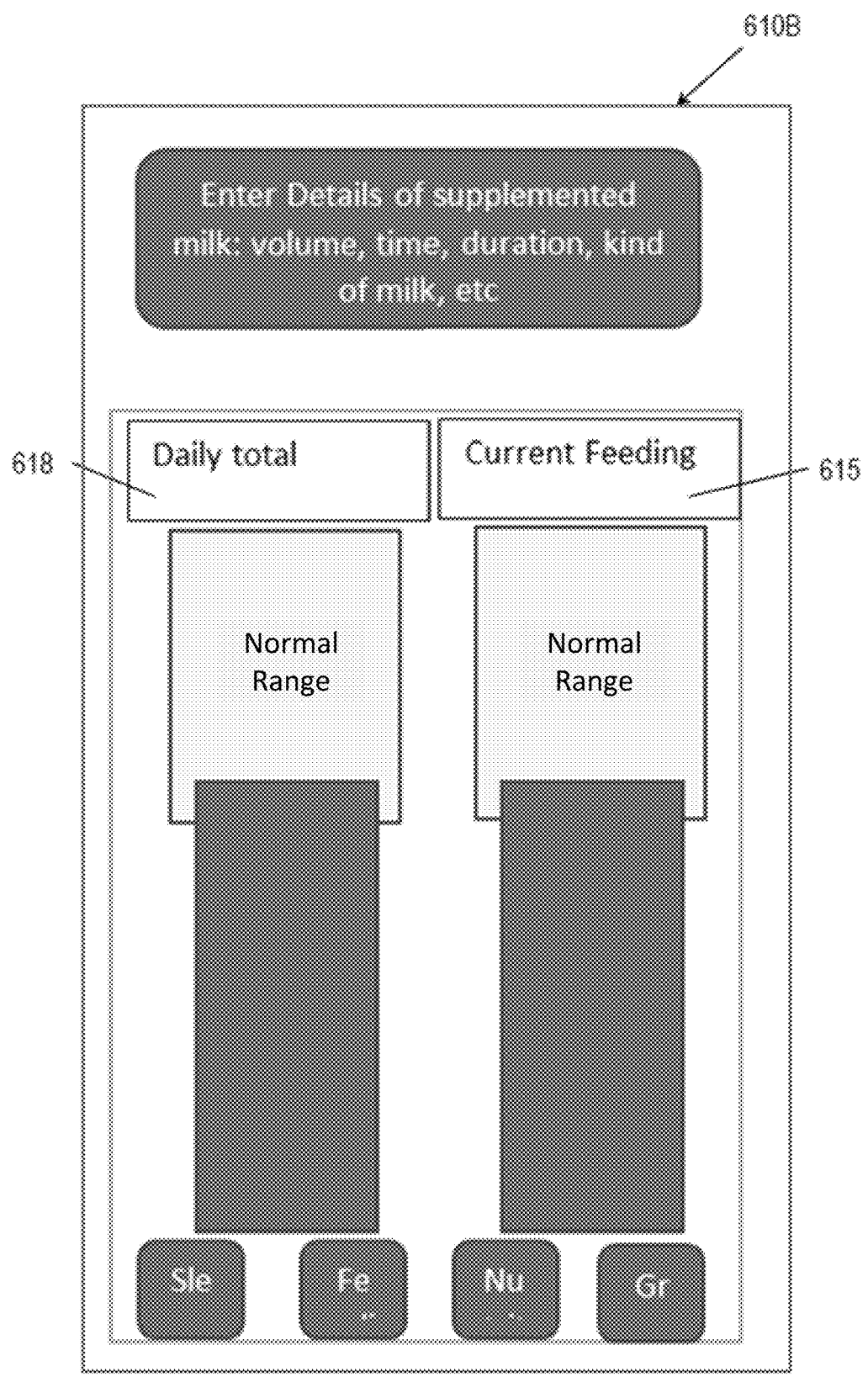
FIG. 3B is a front view of an alternate display incorporating the method of FIG. 1.
Figure 4:
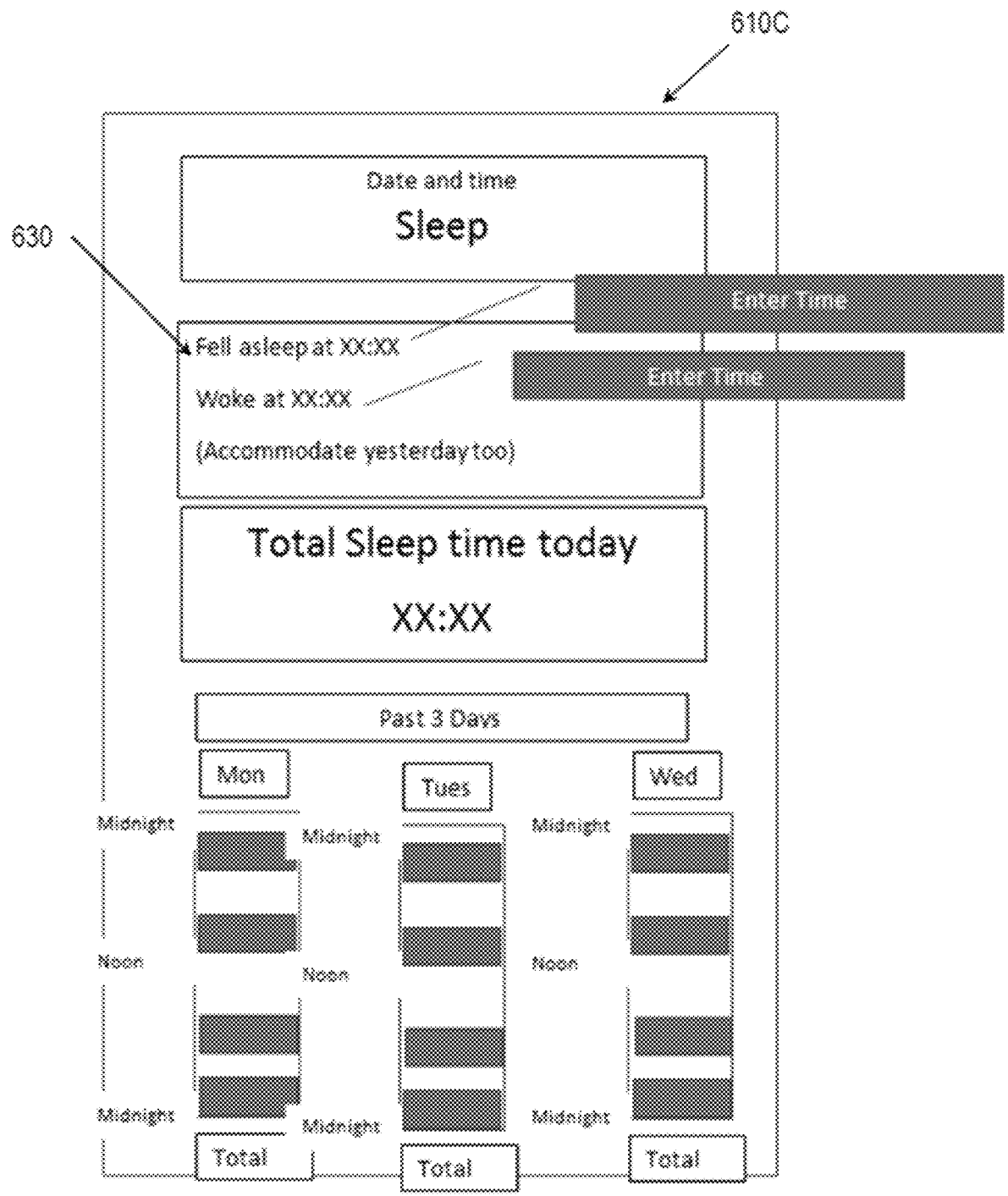
FIG. 4 is a front view of an alternate display incorporating the method of FIG. 1.

FIG. 3A depicts the display 610A of the user device 600. The user device 600 is a smart phone, tablet computer, desktop computer, PDA, or the like. The display 610A depicts a name 612 of the baby, vital statistics 614 of the baby including the weight and height of the baby and the dates of recordation, data regarding the last feeding 616, data regarding the daily total 618, a second data input button 620. The display 610A also depicts a contact list 622, a message indicator 624 and additional interactable menu options for sleep 626, feeding 627, nutrition 628 and growth 629. Additional interactable menu options do not depart from the invention disclosed herein. The user 300 initiates the feeding by selecting the second data input button 620 resulting in a secondary display 610B as depicted in FIG. 3B. The secondary display 610B updates the data regarding the daily total 618 and provides and updates data regarding the current feeding 615. In the display 610C of FIG. 4, the user 300 inputs the second data 630 indicating the time the baby fell asleep and the time the baby woke up. In the embodiment depicted in FIG. 4, the inclusion of the second data 630 allows the display 610C to depict graphical representations of the sleep schedule of the baby. Second data 630 includes a side of the last feeding, a mood of the user, a mood of the baby, an additional sensation information, a weight of the baby, a confidence level of the user, a sleep schedule of the baby, an amount of milk pumped, an amount of milk supplemented, an emergency contact, a physician name, a lactation support contact name, a post-partum depression rating, a rating of support received from the community, and/or a photograph without departing from the invention disclosed herein. The additional sensation information includes, but is not limited to, let-down information, latching information, or other relevant pain information. The method 1000 disclosed herein provides the second data 630 to the device 400 of the expert.

Figure 5:
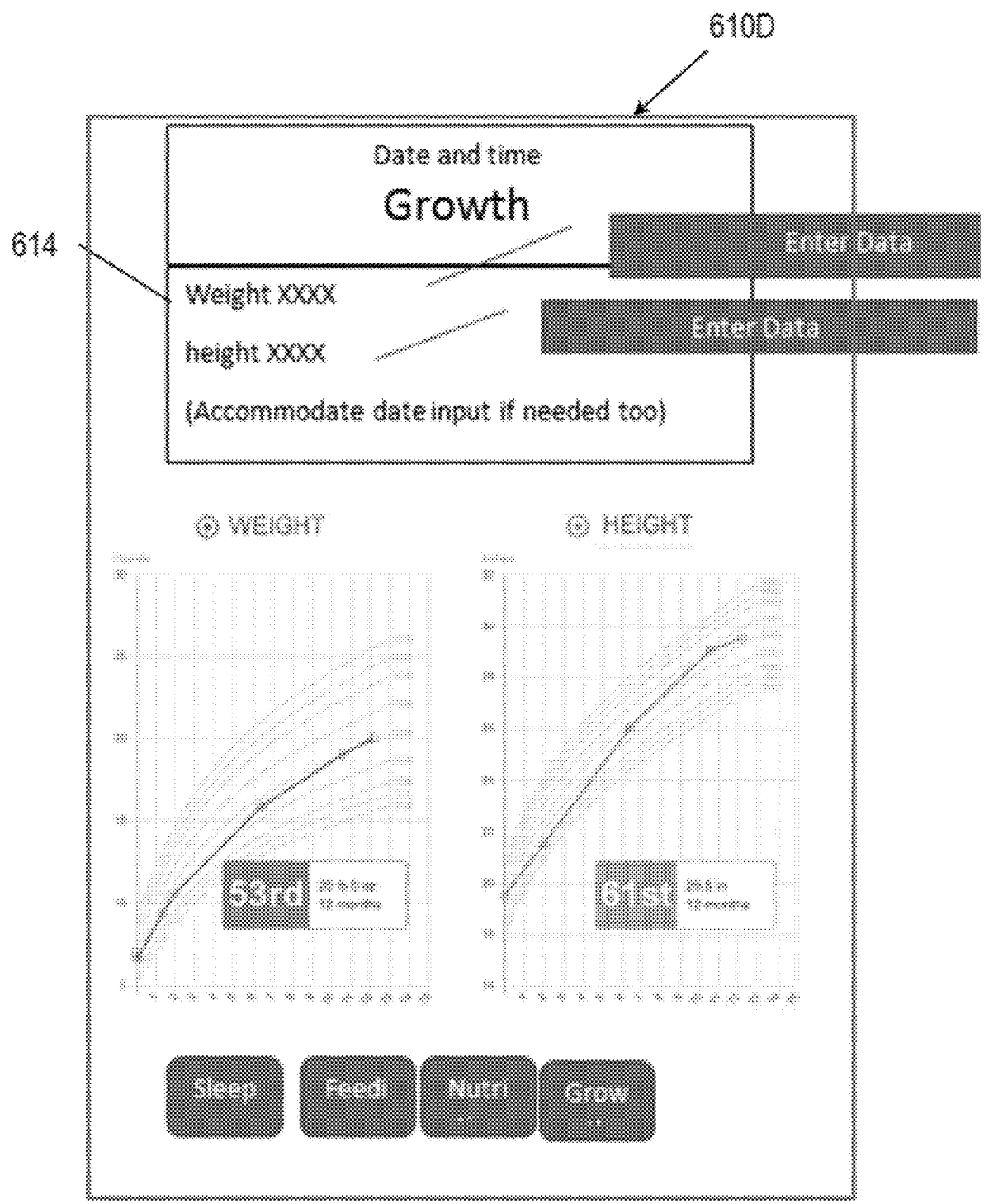
FIG. 5 is a front view of an alternate display incorporating the method of FIG. 1.

Referring to FIG. 5, the display 610D depicts the vital statistics 614 of the baby over time. The user 100 can monitor the vital statistics 614 and the display 610D provides information as to the percentile of the vital statistics 614 and any other relevant information.

Figure 6:
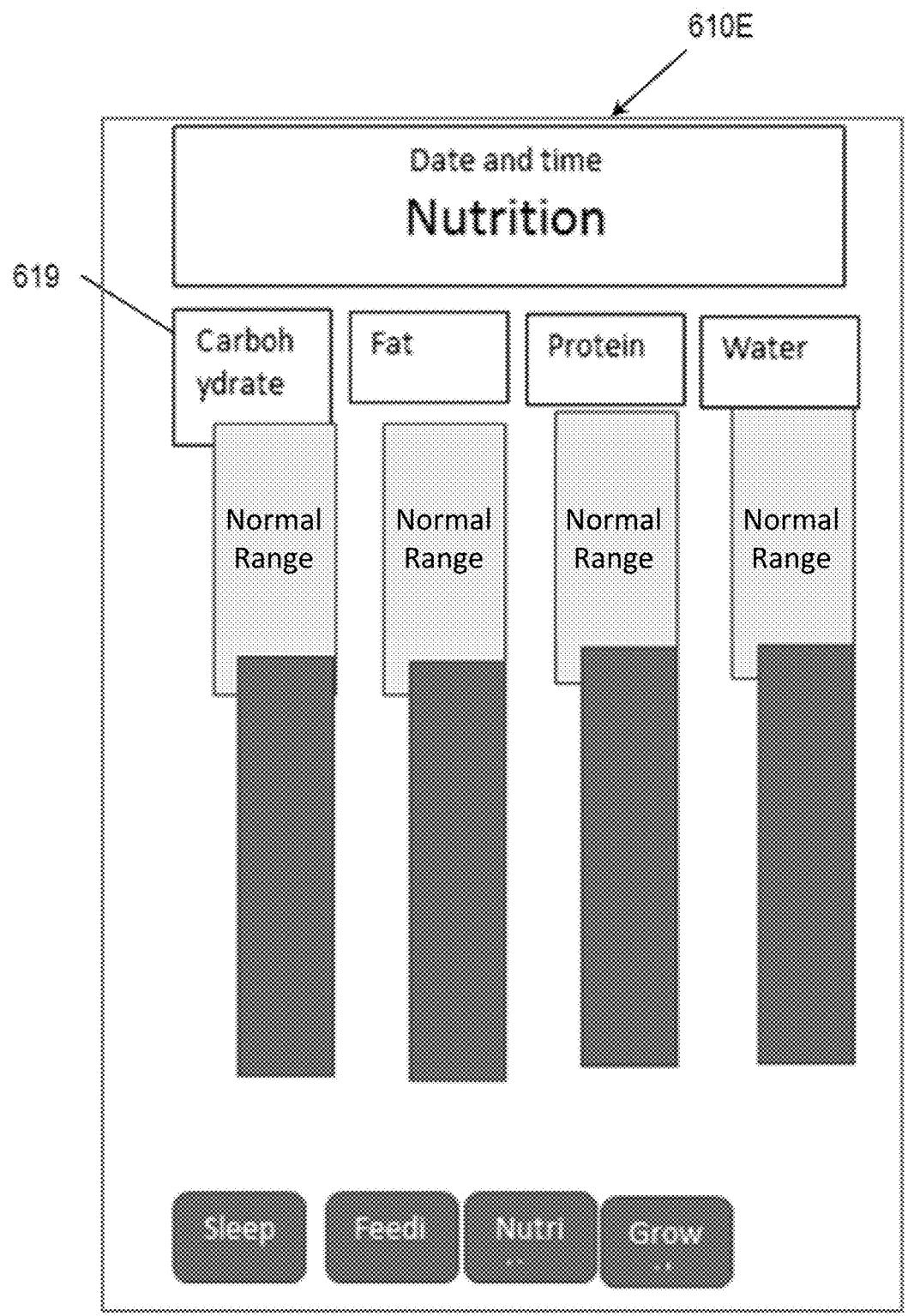
FIG. 6 is a front view of an alternate display incorporating the method of FIG. 1.

Referring to FIG. 6, the display 610E depicts a nutritional content 619 of the breastfeeding event and providing recommendations based on a difference between the nutritional content of the breastfeeding event and the nutritional content of an expected breastfeeding event.

Referring to FIG. 1, the method 1000 also includes creating a predictive model at 170 based on the first data, the second data and/or the lactation transfer report. In one embodiment, the predictive model created at 170 generates an expected next feeding time of the baby. In another embodiment, the predictive model created at 170 generates an additional feeding time for the baby that establishes a necessary time for feeding the baby at the current and/or expected feeding rate to meet a normal feeding amount in the baby. In some embodiments, the normal feeding amount is based on a normalized daily intake of the baby, which is based on the rate of feeding multiplied by the current volume of breast milk in the baby. In some embodiments, the predictive model estimates a fullness of the baby. In some embodiments, the predictive model generates a recommended supplement time for the baby. In one embodiment, the recommended supplement is based on the average feeding amount over a set period (i.e., the previous twenty-four hours) compared to the current feeding amount. The average feeding amount takes into account the expected feeding for a baby of a selected age with a specific weight. This allows the method to evaluate the breastfeeding event and supplement the baby the appropriate amount to meet the normal feeding amount or a desired feeding amount. In some embodiments, the predictive model diagnoses and predicts cluster feedings, growth spurts, illness, and teeth growing. Cluster feeding is identified by comparing the frequency of measured feedings to a normal frequency of feedings. If the method 1000 identifies a cluster feeding at 170, a message informs the user 300 of the cluster feeding and additional information is provided to alleviate any concerns that the user 300 may have. Growth spurts are identified by increases in the number of feedings and/or an increase in the desired volume of milk. If the method 1000 identifies a growth spurt at 170, a message informs the user 300 and additional information is provided to the user 300. Teeth coming in and/or other illnesses are identified by observing patterns in the feedings and/or through decreases in the number, duration or rate of the feedings. If illnesses and/or teeth coming in are identified, the method 1000 generates a message to encourage the user 300 to continue feeding and providing suggestions for further support. Other predictive models based on breastfeeding data analytics as known to a person of ordinary skill in the relevant art do not depart from the invention disclosed herein.

The method 1000 depicted in FIG. 1 also includes providing a feedback indicator 620 (depicted in FIG. 2) to the user 300 at 180. The feedback indicator 612 displays lights or other wording that indicates a normal filling rate, an abnormal filling rate, a normal time of feeding, an abnormal time of feeding, a normal volume of feed, an abnormal volume of feed, a normal frequency of feed and an abnormal frequency of feed. The method 1000 also includes warning the user 300 at 190 if the feedback indicator 620 denotes an abnormal filling rate, an abnormal time of feeding, an abnormal volume of feed and/or an abnormal frequency of feed. For example, in some embodiments the feedback indicator 612 alerts, "Infant has received less than XX mL in the last twenty-four hours," "The mother's rate of production is abnormally low," etc. The feedback indicator 612 informs the user 300 if the breastfeedings are progressing in a normal manner or if the user 300 should seek support from experts. The method 1000 depicted in FIG. 1 also includes notifying the user and/or the expert with a warning at 195. The method 1000 notifies the user and/or the expert with a warning at 195 that is an initial warning or an imminent trouble warning. The initial warning advises the user or expert to seek additional support and the imminent trouble warning provides recommendations for triage and emergency support. The initial warning seeks professional support by providing contact information for an expert, including but not limited to, a doctor, a nurse, or a lactation support person stored within the database 111 or otherwise recommended by the method 1000. The imminent trouble warning provides immediate assistance in contacting emergency services (i.e., dialing 9-1-1 or making an emergency call to a physician, etc.).

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of monitoring lactation transfer information from a user to a baby, the method comprising:
receiving a first data from at least one detector configured to measure a lactation transfer information of a breastfeeding event between the user and the baby;
receiving a second data from a user device;
processing the first data and the second data to create a lactation transfer report;
communicating the lactation transfer report to at least one of the user device and a device accessible by one or more experts; and
providing feedback to the user based on at least one of the first data, the second data and the lactation transfer report,
wherein the first data comprises at least one of a time of the breastfeeding event, a length of the breastfeeding event and a rate of filling of the breastfeeding event,
wherein the user device receives the second data from the user, and
wherein the step of providing feedback comprises providing at least one of an emergency contact, a physician name and a lactation support contact name based on the one or more experts evaluation of at least one of the first data, the second data and the lactation transfer report.

2. The method according to claim 1, wherein the second data comprises at least one of a side of the last feeding, a mood of the user, a mood of the baby, an additional sensation information, a weight of the baby, a confidence level of the user, a sleep schedule of the baby, an amount of milk pumped, an amount of milk supplemented, a post-partum depression rating, a rating of support received from the community and a photograph.

3. The method according to claim 2, wherein the additional sensation information comprises let-down information, latching information or pain information.

4. The method according to claim 1, wherein the first data comprises at least one of an initial volume of milk in a stomach of the baby, a volume of milk transferred to the baby and a residual amount of milk in stomach of the baby.

5. The method according to claim 1, comprising:
automatically selecting relevant information from a database based on at least one of the first data, the second data and the lactation transfer report; and
providing the relevant information to at least one of the user and the one or more experts.

6. The method according to claim 1, comprising recording at least one of the first data, the second data and the lactation transfer report in a medical record of the user.

7. The method according to claim 1, comprising providing a notification to at least one of the one or more experts and the user based on at least one of the first data, the second data and the lactation transfer report.

8. The method according to claim 1, comprising at least one of scheduling and altering an appointment of the user and one or more experts based on at least one of the first data, the second data and the lactation transfer report.

9. The method according to claim 1, wherein the user device comprises a display and the user and the one or more experts directly communicate through the display of the user device.

10. The method according to claim 1, comprising communicating at least one of the first data, the second data and the lactation transfer report to a designated recipient selected by the user.

11. The method according to claim 1, comprising evaluating a nutritional content of the breastfeeding event and providing recommendations based on a difference between the nutritional content of the breastfeeding event and the nutritional content of an expected breastfeeding event.

12. A method of monitoring lactation transfer information from a user to a baby, the method comprising:
receiving a first data from at least one detector configured to measure lactation transfer information of a breastfeeding event between the user and the baby;
receiving a second data from a user device;
processing the first data and the second data to create a lactation transfer report;

communicating the lactation transfer report to at least one of the user device and a device accessible by one or more experts;

generating a feedback indicator based on at least one of the first data, the second data, the lactation transfer report, an input received from the user and an input received from the one or more experts;

providing the feedback indicator to the user device, the feedback indicator comprising at least one of normal filling rate, abnormal filling rate, normal time of feeding, abnormal time of feeding, normal volume of feed, abnormal volume of feed, normal frequency of feed and abnormal frequency of feed; and notifying at least one of the user and one or more experts with a warning based on at least one of the first data, the second data and the lactation transfer report, wherein the first data comprises at least one of a time of the breastfeeding event, a length of the breastfeeding event and a rate of filling of the breastfeeding event, wherein the user device receives the second data from the user, wherein the warning comprises an initial warning or an imminent trouble warning, wherein the initial warning advises the user or expert to seek additional support, and wherein the imminent trouble warning provides recommendations for triage and emergency support.

* * * * *